(12) United States Patent
McClunan (10) Patent No.: US 11,058,580 B2
(45) Date of Patent: Jul. 13, 2021

(54) ORBITAL TISSUE RETRACTOR

(71) Applicant: Liqid Medical Proprietary Limited, Cape Town (ZA)

(72) Inventor: Daemon Bruce McClunan, Cape Town (ZA)

(73) Assignee: Liqid Medical Proprietary Limited, Cape Town (ZA)

( * ) Notice: Subject to any disclaimer, the term of this patent is extended or adjusted under 35 U.S.C. 154(b) by 0 days.

(21) Appl. No.: 16/342,372

(22) PCT Filed: Nov. 2, 2017

(86) PCT No.: PCT/IB2017/056816
§ 371 (c)(1),
(2) Date: Apr. 16, 2019

(87) PCT Pub. No.: WO2018/083619
PCT Pub. Date: May 11, 2018

(65) Prior Publication Data
US 2019/0261972 A1    Aug. 29, 2019

(30) Foreign Application Priority Data
Nov. 2, 2016   (ZA) .................................. 2016/07546

(51) Int. Cl.
*A61F 9/007*      (2006.01)
*A61B 17/02*     (2006.01)
(Continued)

(52) U.S. Cl.
CPC ...... *A61F 9/00781* (2013.01); *A61B 1/00154* (2013.01); *A61B 17/0231* (2013.01);
(Continued)

(58) Field of Classification Search
CPC ......... A61B 17/023; A61B 1/32; A61B 17/02; A61B 17/0218; A61B 17/0231; A61F 9/00781; A61F 9/007
(Continued)

(56) References Cited

U.S. PATENT DOCUMENTS

| 6,267,752 B1 | 7/2001 | Svetliza | |
|---|---|---|---|
| 2014/0277429 A1* | 9/2014 | Kuzma | ............... A61F 9/0017 623/4.1 |
| 2016/0015467 A1* | 1/2016 | Vayser | ................ A61B 90/30 600/245 |

FOREIGN PATENT DOCUMENTS

| EP | 1 029 508 A1 | 8/2000 |
|---|---|---|
| WO | 2003053229 A2 | 7/2003 |

OTHER PUBLICATIONS

International Search Report and Written Opinion dated Feb. 15, 2018 for International Application No. PCT/IB2017/056816, entitled "Orbital Tissue Retractor".

* cited by examiner

*Primary Examiner* — Matthew J Lawson
*Assistant Examiner* — Lisa Nguyen
(74) *Attorney, Agent, or Firm* — Hamilton, Brook, Smith & Reynolds, P.C.

(57) ABSTRACT

An orbital tissue retractor 10 for use in a surgical operation in the region of an eye socket, comprises an orbital tissue retractor body 12 and a handle 14 extending therefrom for manipulation of the tissue retractor body by a surgeon. The tissue retractor body comprises a channel formation 16 defining a channel 17. The channel formation 16 has a pair of spaced side wall sections 24 which define concave curved ocular abutment formations 26 which conform to an anatomical curvature of the ocular globe for abutment with the ocular globe N. The tissue retractor body has open proximal (Continued)

end 22 and an open distal end 20. The tissue retractor body tapers from the proximal end to the distal end, with a portion of the channel formation at the distal end being curved so as to accommodate and cradle the optic nerve therein. The retractor body has a curved base wall section 28 conforming to an anatomical curvature of the orbit.

16 Claims, 13 Drawing Sheets

(51) Int. Cl.
    *A61B 1/00*     (2006.01)
    *A61B 3/00*     (2006.01)
    *A61F 9/00*     (2006.01)

(52) U.S. Cl.
    CPC ................ *A61F 9/007* (2013.01); *A61B 3/00* (2013.01); *A61F 2009/0052* (2013.01); *A61M 2210/0612* (2013.01)

(58) Field of Classification Search
    USPC ........................................................ 600/236
    See application file for complete search history.

ORBITAL TISSUE RETRACTOR

This application is the U.S. National Stage of International Application No. PCT/IB2017/056816, filed Nov. 2, 2017, which designates the U.S., published in English, and claims priority under 35 U.S.C. § 119 or 365(c) to South Africa Application No. 2016/07546, filed Nov. 2, 2016. The entire teachings of the above applications are incorporated herein by reference.

FIELD OF INVENTION

The invention relates to the field of surgical instruments. More specifically, the invention relates to a tissue retractor for use in surgery in the region of an eye socket. Because the eye socket is also referred to as an orbit, such retractors are known as orbital tissue retractors.

BACKGROUND TO INVENTION

Surgical operations involving the orbital portion of the optic nerve are procedures which require adequate visualisation of, and access to, the optic nerve. For such procedures, orbital tissue retractors are used which need to perform the following functions in order to be effective: define a passageway in orbital tissue having a proximal opening externally of the orbit and a distal opening adjacent the optic nerve, displace orbital tissues away from the passageway, prevent orbital fat prolapse into the passageway, allow the orbital optic nerve to enter the distal opening of the passageway, and prevent conjunctival tissue from obscuring the proximal opening of the passageway.

The orbit is predominantly comprised of the following structures: the cone-shaped bony orbit referred to as the orbital cone, the ocular globe positioned near a base of the orbital cone, four extraocular rectus muscles which pass from an apex of the orbital cone to insert on the anterior half of the ocular globe, the optic nerve which passes from the apex of the orbital cone to insert near a posterior pole of the ocular globe, the orbital fat, and the tenon's capsule which lies between the ocular globe and the orbital fat. The orbital optic nerve is surrounded by a sheath of dura mater. The subarachnoid space lies between the optic nerve and its sheath and is filled with cerebrospinal fluid.

Optic nerve sheath fenestration is a surgical procedure which involves exposure of the optic nerve and fenestration of the sheath using a surgical blade. In this procedure, cerebrospinal fluid is released from the subarachnoid space and transmission of cerebrospinal fluid pressure to the optic nerve head is reduced. Optic nerve sheath fenestration is used to ameliorate visual loss associated with raised intracranial pressure.

Oculo-subarachnoid shunting is a surgical procedure which involves exposure of the optic nerve and the implantation of a shunt system which connects the subarachnoid space and the ocular globe. An oculo-subarachnoid shunt system provides for the regulation of intraocular pressure to ameliorate ocular diseases associated with disorders of intraocular or intracranial pressure.

Current known orbital tissue retractors are able only to displace orbital tissues along one tissue plane. This means that multiple retractors and therefore multiple surgeons are usually required to define a clear passageway to the optic nerve. Furthermore, known orbital tissue retractors are not configured to accommodate the optic nerve. As a result, orbital fat tends to prolapse into the passageway, causing difficulties with surgical access to, and visualisation of the optic nerve.

It is an object of the present invention to provide an orbital tissue retractor which ameliorates the abovementioned difficulties associated with eye surgery where access to the orbital portion of the optic nerve is required.

SUMMARY OF INVENTION

According to the invention there is provided an orbital tissue retractor for use in a surgical operation in the region of an eye socket, the orbital tissue retractor including an orbital tissue retractor body which is formed for abutment with the ocular globe of the eye so as to displace orbital tissue from the orbital globe and which defines a passageway for a surgical instrument between the displaced orbital tissue and the ocular globe, the tissue retractor body having an open proximal end and an open distal end, the orbital tissue retractor body defining a channel formation at least at a distal end region thereof which is configured so as to accommodate the optic nerve therein.

The distal end region of the orbital tissue retractor body may be dimensioned so as to receive and cradle the optic nerve sheath therein.

The channel formation of the orbital tissue retractor body may have a curvature which conforms to the curvature of the optic nerve sheath permitting the optic nerve sheath to be received therein.

The channel formation of the orbital tissue retractor body may have a C-shaped configuration when viewed in cross-sectional end view.

The orbital tissue retractor body may be dimensioned so as to be received within the orbit.

The orbital tissue retractor body may have a curved configuration conforming to an anatomical curvature of the orbit.

The channel formation of the orbital tissue retractor body may have a pair of spaced wall sections defining concave curved ocular abutment formations for abutment with the ocular globe.

The ocular abutment formations of the orbital tissue retractor body may have curvatures which conform to an anatomical curvature of the ocular globe.

The channel formation may have a base wall section extending between the side wall sections, the base wall section having a first curvature at least at a distal end region of the orbital tissue retractor body, extending in a direction between the side wall sections, when viewed in cross-sectional end view, which conforms to an anatomical curvature of the orbital rim of the orbit.

The base wall section of the channel formation may have a second curvature extending between the proximal and distal ends of the orbital tissue retractor body, when viewed in side view, which conforms to an anatomical curvature of the ocular globe.

The proximal end of the orbital tissue retractor body may be relatively wider than the distal end thereof.

The orbital tissue retractor body may taper from the proximal end thereof towards the distal end thereof.

The channel formation of the orbital tissue retractor body may extend from the proximal end to the distal end thereof.

The orbital tissue retractor may include a handle extending from the orbital tissue retractor body which can be held for manipulating the orbital tissue retractor body. More specifically, the handle of the orbital tissue retractor may extend from the proximal end of the tissue retractor body.

The orbital tissue retractor body may include an outwardly flared collar formation at the proximal end thereof, which is formed so as to prevent conjunctival tissue from prolapsing into the passageway and thereby obscuring the passageway, in use.

The orbital tissue retractor body may have a tubular formation having a hollow tubular configuration at a proximal end region thereof, with the distal end region defining the channel formation, the passageway being defined by the tubular formation and the channel formation.

The tubular formation may include a support formation for supporting an endoscope. More specifically, the support formation may be in the form of an internal passage defined within the tubular formation, within which the endoscope is received and supported.

BRIEF DESCRIPTION OF THE DRAWINGS

Further features of the invention are described hereinafter by way of a non-limiting example of the invention, with reference to and as illustrated in the accompanying diagrammatic drawings. In the drawings.

DETAILED DESCRIPTION OF THE INVENTION

Figure 1:
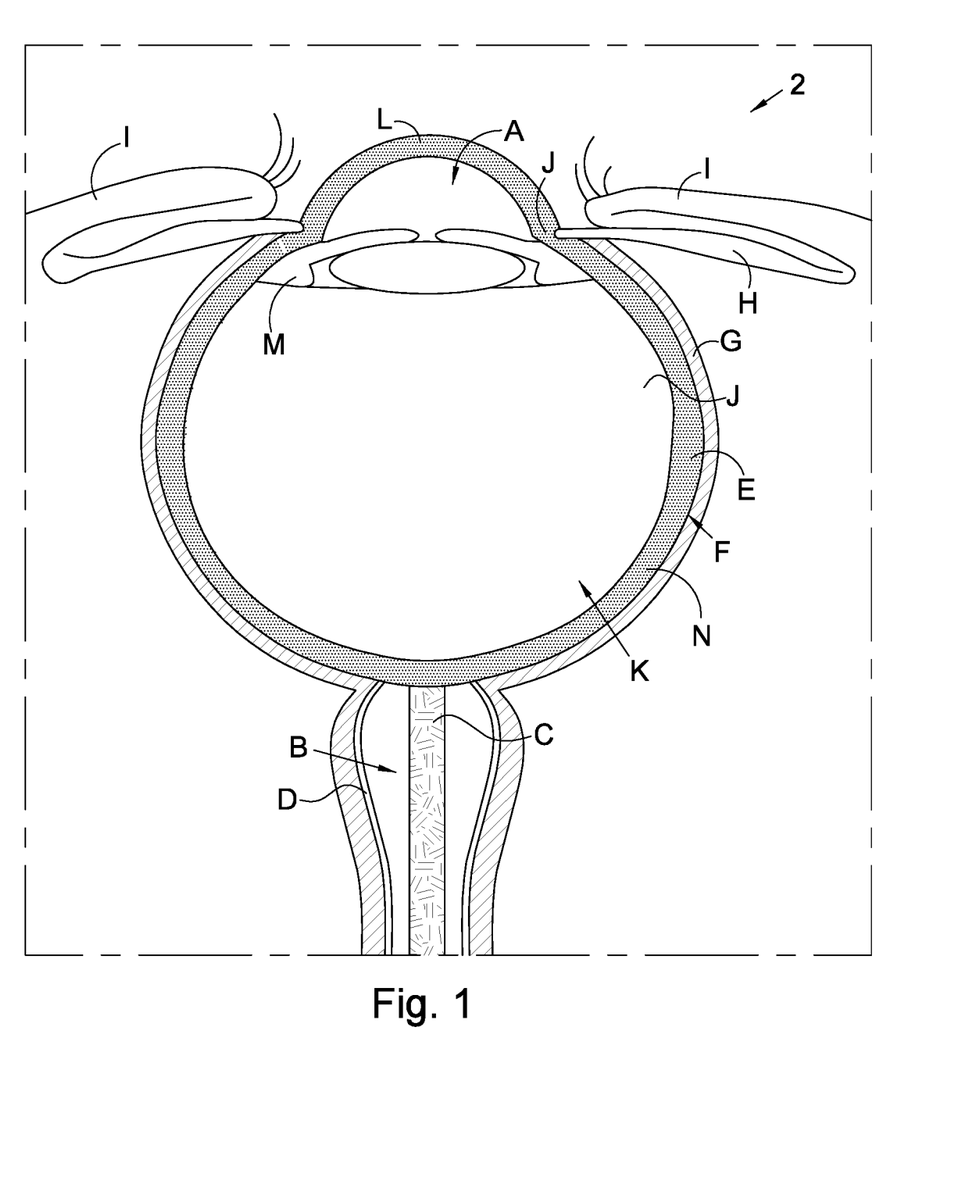
FIG. 1 shows a cross-sectional view of a human eye.
Figure 2:
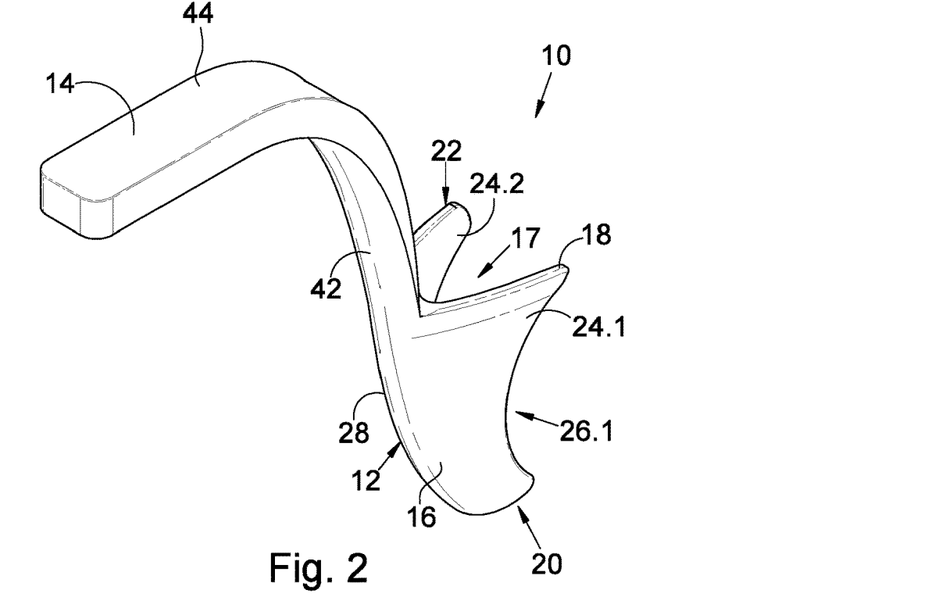
FIG. 2 shows a three-dimensional view of a first embodiment of an orbital tissue retractor in accordance with the invention.
Figure 3:
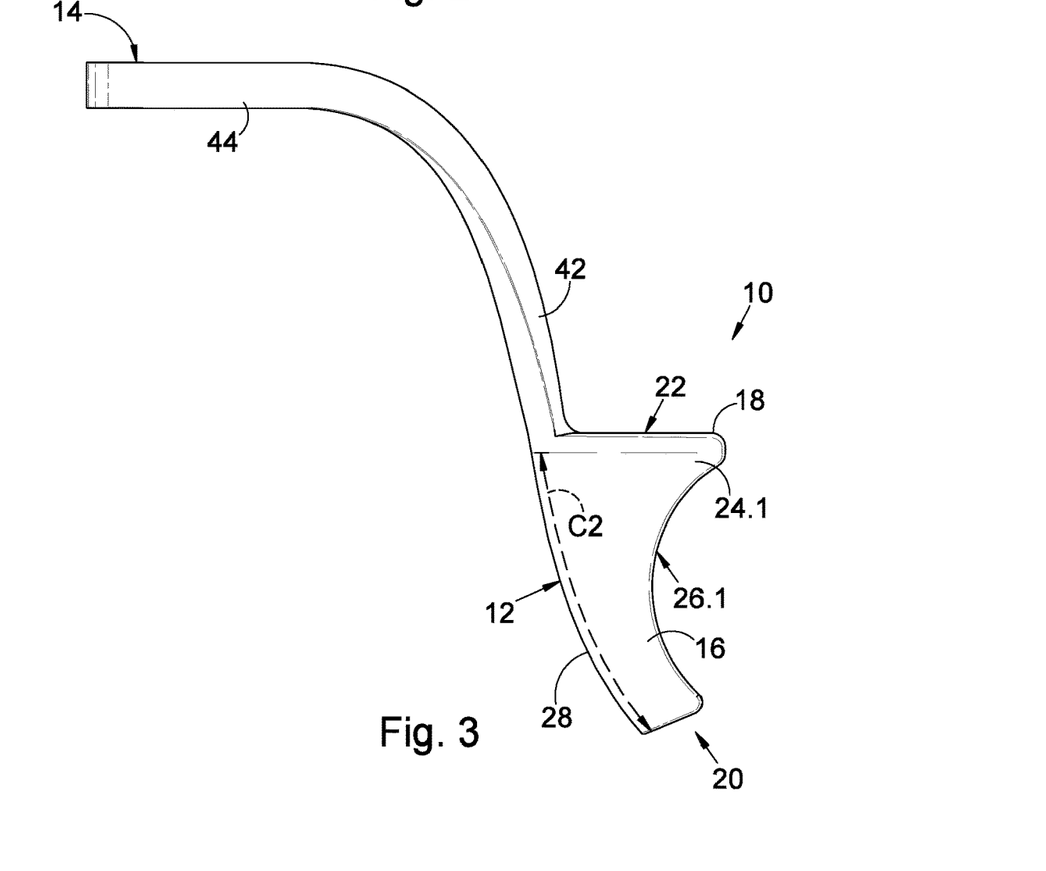
FIG. 3 shows a side view of the orbital tissue retractor of FIG. 2.
Figure 4:
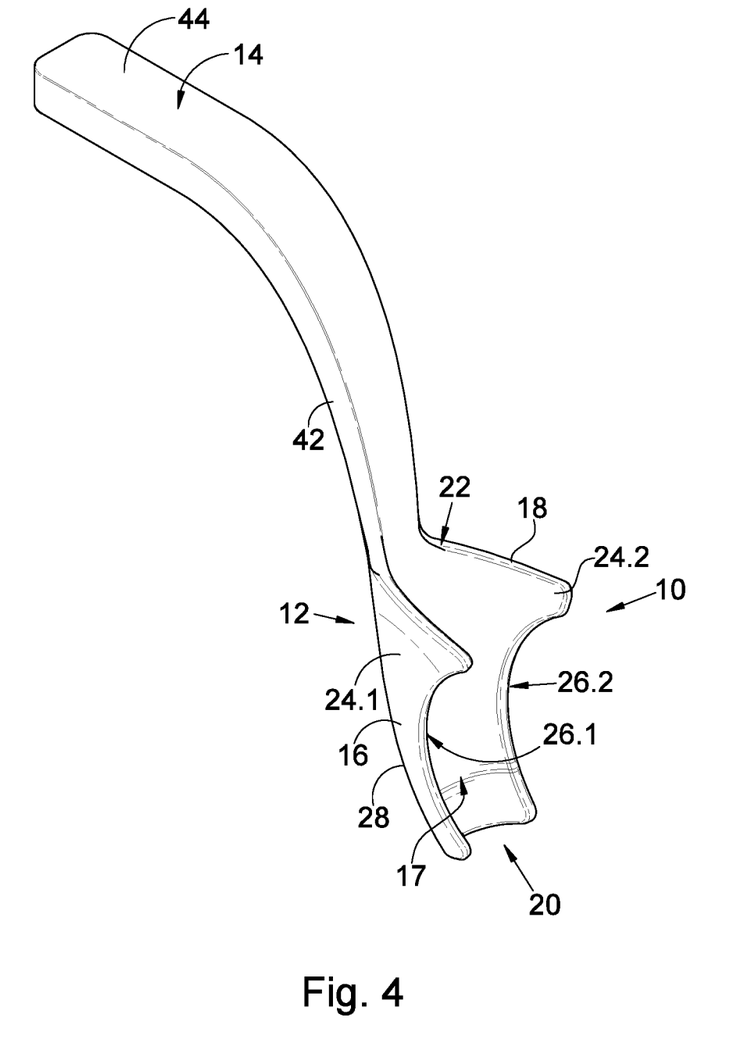
FIG. 4 shows an opposite side view of the orbital tissue retractor of FIG. 2.
Figure 5:
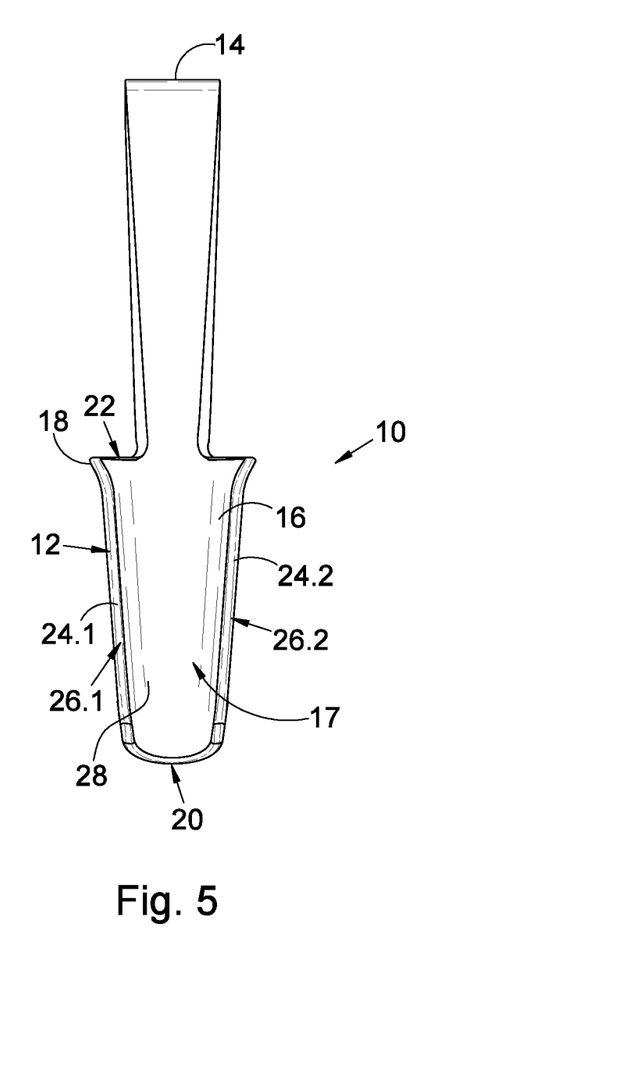
FIG. 5 shows a front view of the orbital tissue retractor of FIG. 2.
Figure 6:
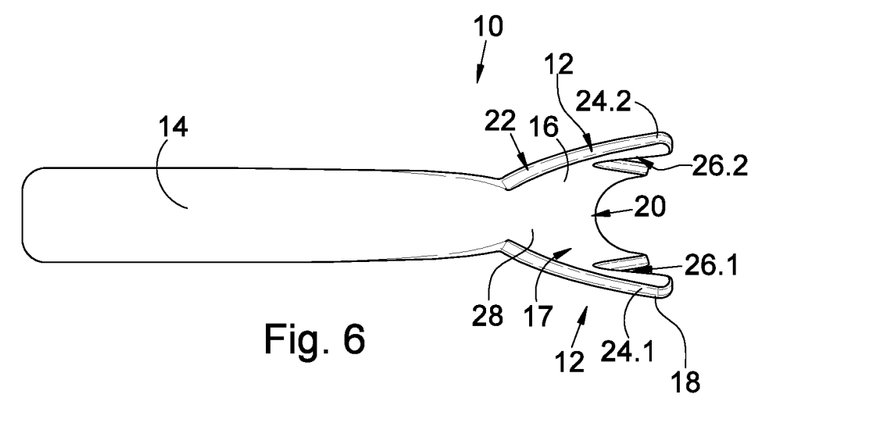
FIG. 6 shows a top plan view of the orbital tissue retractor of FIG. 2.
Figure 7:
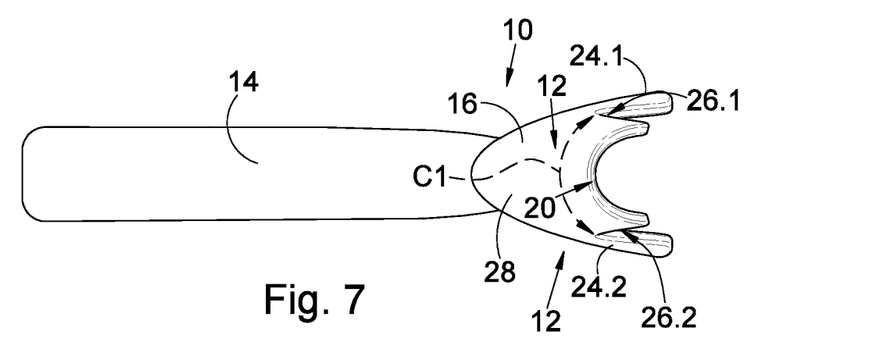
FIG. 7 shows a bottom plan view of the orbital tissue retractor of FIG. 2.

With reference to FIG. 1 of the drawings, a cross-sectional view illustrating anatomical parts of a human eye 2 which are required for use in the description which follows below, comprises:

A: Anterior chamber filled with aqueous fluid
B: Subarachnoid space filled with cerebrospinal fluid
C: Optic nerve
D: Optic nerve sheath
E: Sclera
F: Subtenon's space
G: Tenon's capsule
H: Conjunctiva
I: Eyelids
J: Limbus and trabecular meshwork
K: Posterior segment filled with vitreous jelly
L: Cornea
M: Ciliary body
N: Ocular globe With reference to FIGS. 2 to 9 of the drawings, a first embodiment of an orbital tissue retractor in accordance with the invention, is designated by the reference numeral 10. The orbital tissue retractor is used for creating a passageway through orbital connective tissue surrounding the ocular globe N and the optic nerve sheath D and comprises an orbital tissue retractor body 12 and a handle 14 which extends from the orbital tissue retractor body for manipulating the retractor body. The orbital tissue retractor body comprises a channel formation 16 which defines a channel 17. The orbital tissue retractor body 12 has an open-ended C-shaped configuration when viewed in cross-sectional end view, with the orbital tissue retractor body having a relatively narrower distal insertion end 20 and a relatively wider proximal end 22. The orbital tissue retractor body has a generally tapered configuration wherein the tissue retractor body tapers from the proximal end thereof to the distal end thereof. The taper allows for easier insertion of the orbital tissue retractor body into orbital connective tissue.

The channel formation 16 has a pair of spaced side wall sections 24.1 and 24.2 for spacing orbital connective tissue from the ocular globe and the optic nerve sheath so as to create the passageway. End regions of the side wall sections 24.1, 24.2 define curved ocular abutment formations 26.1 and 26.2, respectively, for abutment with the ocular globe of the eye. The ocular abutment formations 26 have concave curved configurations conforming to the anatomical curvature of ocular globe. Furthermore, the distal end of the tissue retractor body is dimensioned and curved so as to conform to the anatomical shape of the optic nerve sheath so as to permit the optic nerve sheath to be received and cradled therein.

The channel formation 16 has a curved configuration which conforms to the curvature of the orbit. The channel formation has a base wall section 28 extending between the side wall sections. The base wall section 28 has a first curved surface C1 extending between the side wall sections, when viewed in cross-sectional end view, which conforms to an anatomical curvature of the orbital rim of the cone-shaped orbit. The base wall section 28 has a second curved surface C2 extending between the proximal and distal ends of the orbital tissue retractor body, when viewed in side view, which conforms to an anatomical curvature of the ocular globe. The curvature of the second curved surface partly provides the orbital tissue retractor body with its tapered configuration reducing the distance between the base wall of the orbital tissue retractor body and the ocular globe when the distal end region of the orbital tissue retractor body is positioned within the orbit. The first and second curved surfaces of the base wall section of the tissue retractor wall, extend orthogonally relative to one another.

The orbital tissue retractor body 12 defines an outwardly flared collar 18 at the proximal end thereof. The collar 18 is configured and dimensioned so as to prevent conjunctival tissue from prolapsing and thereby obscuring the passageway, in use.

The handle 14 is integrally formed with the orbital tissue retractor body 12 and includes a first section 42 which extends operatively upwardly from the base wall section 28, at the proximal end 22 of the orbital tissue retractor body 16 and a second section 44 which extends laterally outwardly from the first section so that the second section of the handle projects away from the orbit when an operation is performed on the eye by a surgeon holding the handle.

Figure 9:
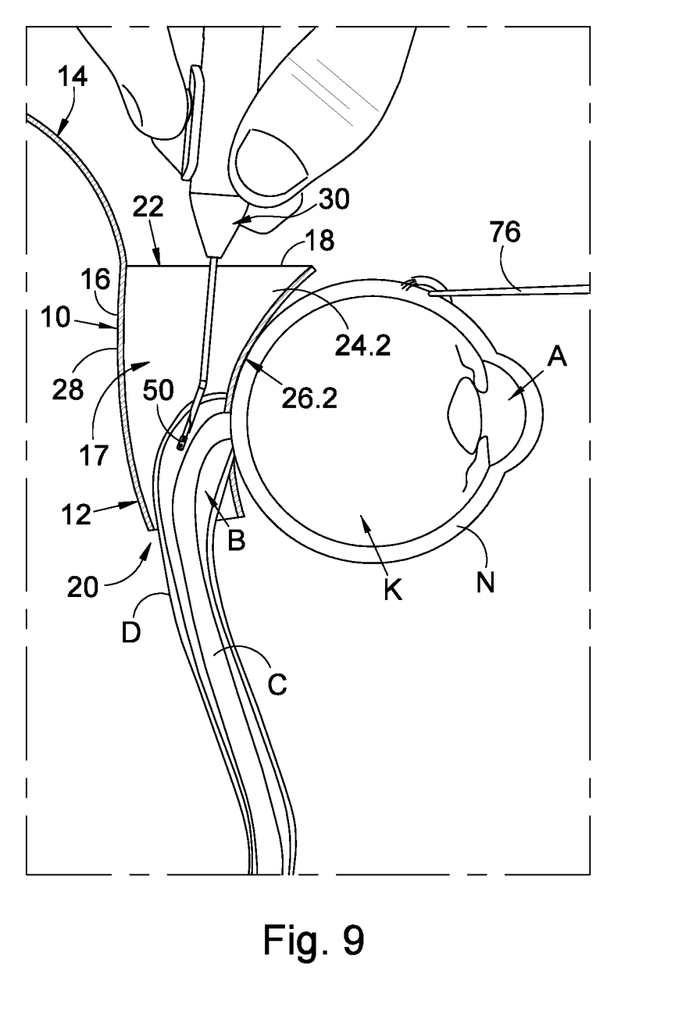
FIG. 9 shows the manner in which the orbital tissue retractor of FIG. 2 defines a passageway in orbital tissue for receiving a shunt inserting device in a surgical procedure for the insertion of a shunt extending between the subarachnoid space of the optic nerve and an anterior chamber of the eye.

The orbital tissue retractor 10 may be used for the insertion of a shunt insertion device 30 for use in the implantation of a shunt 50 providing for flow communication between aqueous fluid in the anterior chamber A of the eye and cerebrospinal fluid in the subarachnoid space B surrounding the optic nerve C. The shunt, when implanted, regulates intraocular pressure in the eye of a human patient. When positioned in abutment with the ocular globe and the optic nerve sheath, the orbital tissue retractor body defines the passageway within which a shunt insertion device 30 and the shunt 50, is received.

Figure 8A:
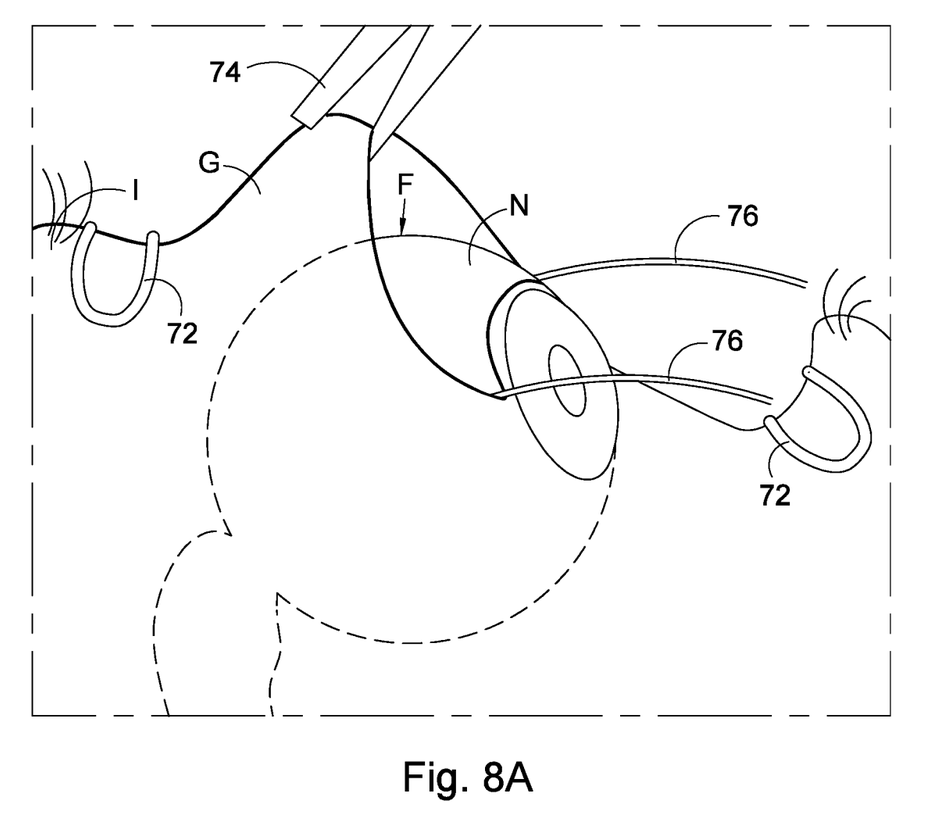
FIGS. 8A to 8E shows, in sequence, the manner in which the orbital tissue retractor of FIG. 2 is inserted into orbital tissue surrounding the ocular orbit.
Figure 8B:
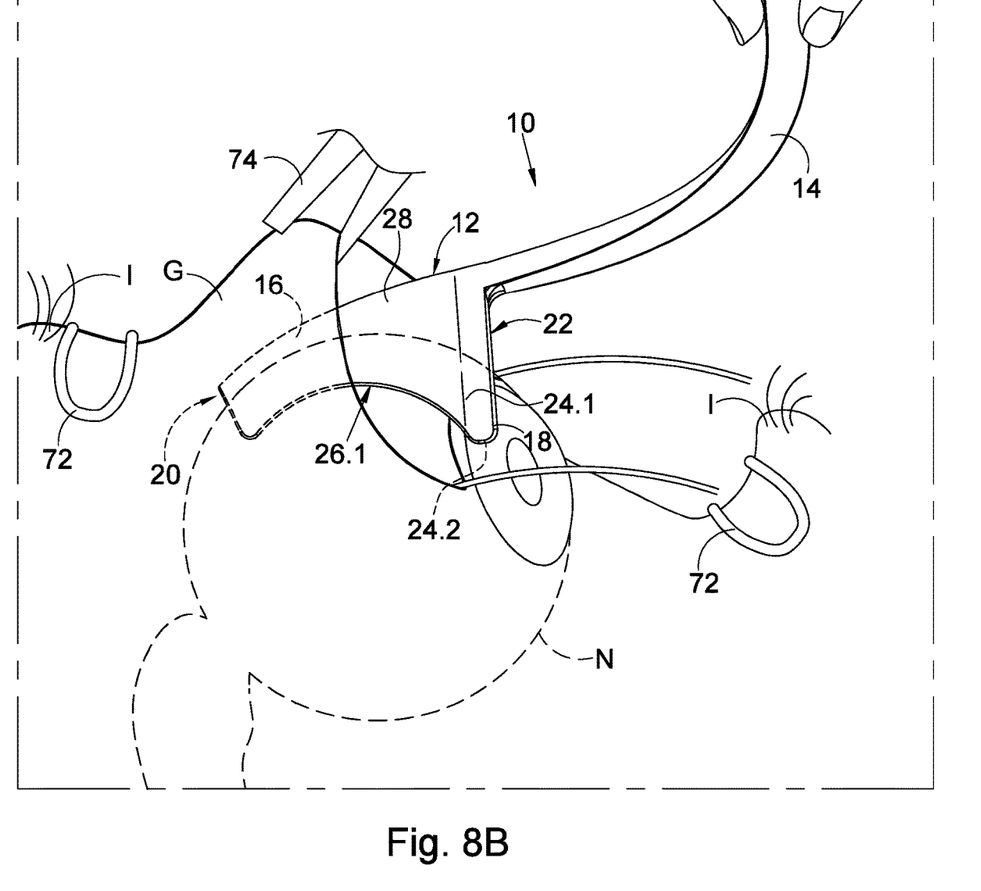
Figure 8C:
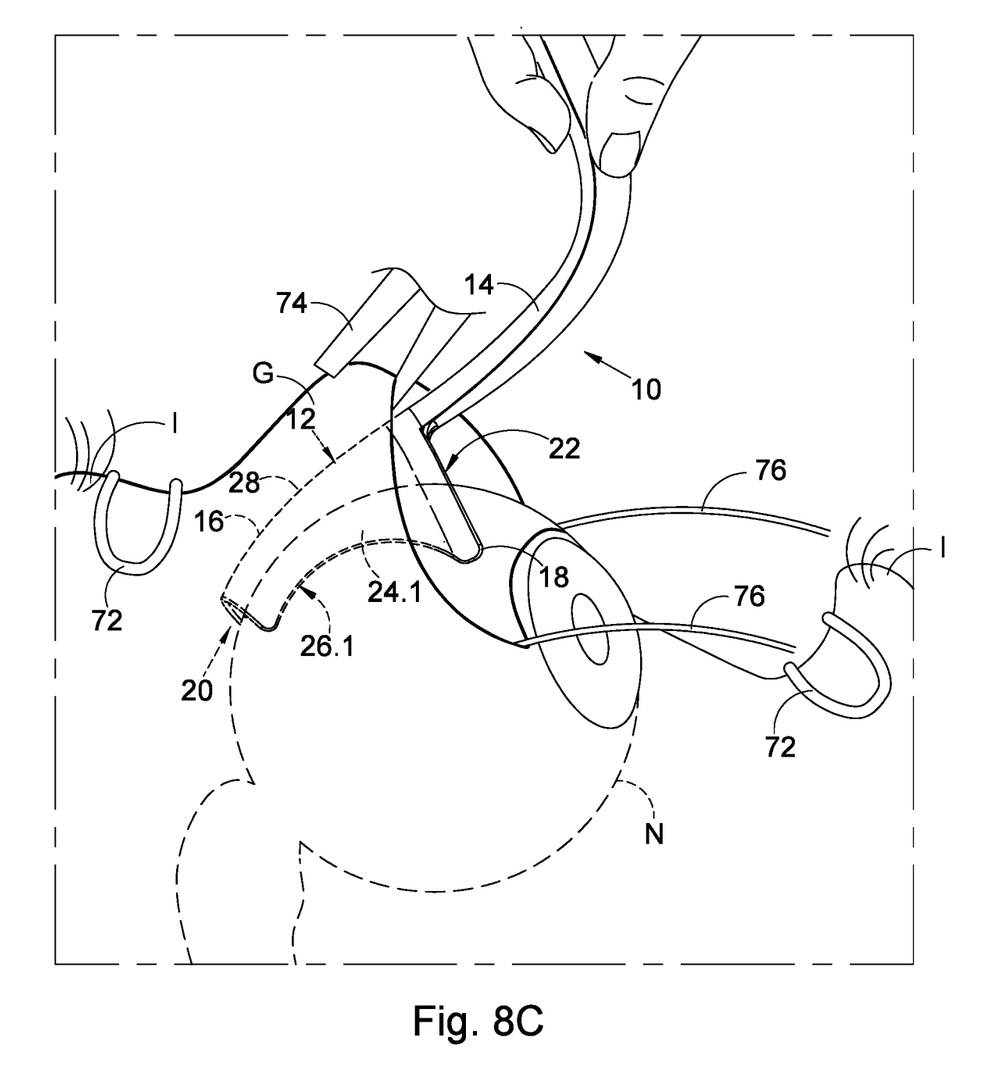
Figure 8D:
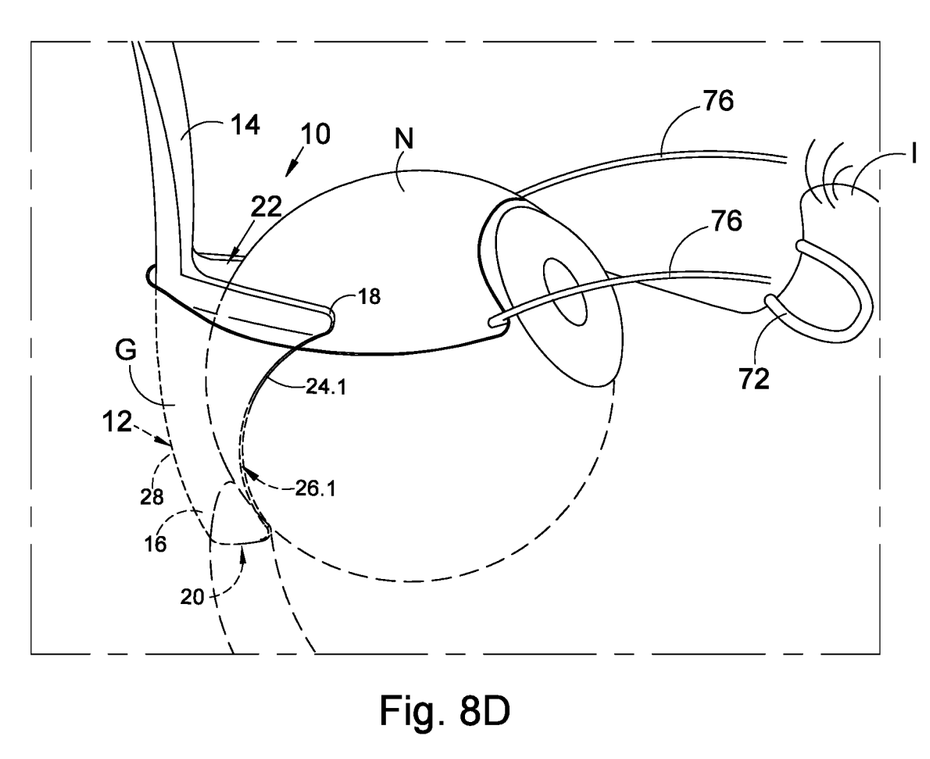
Figure 8E:
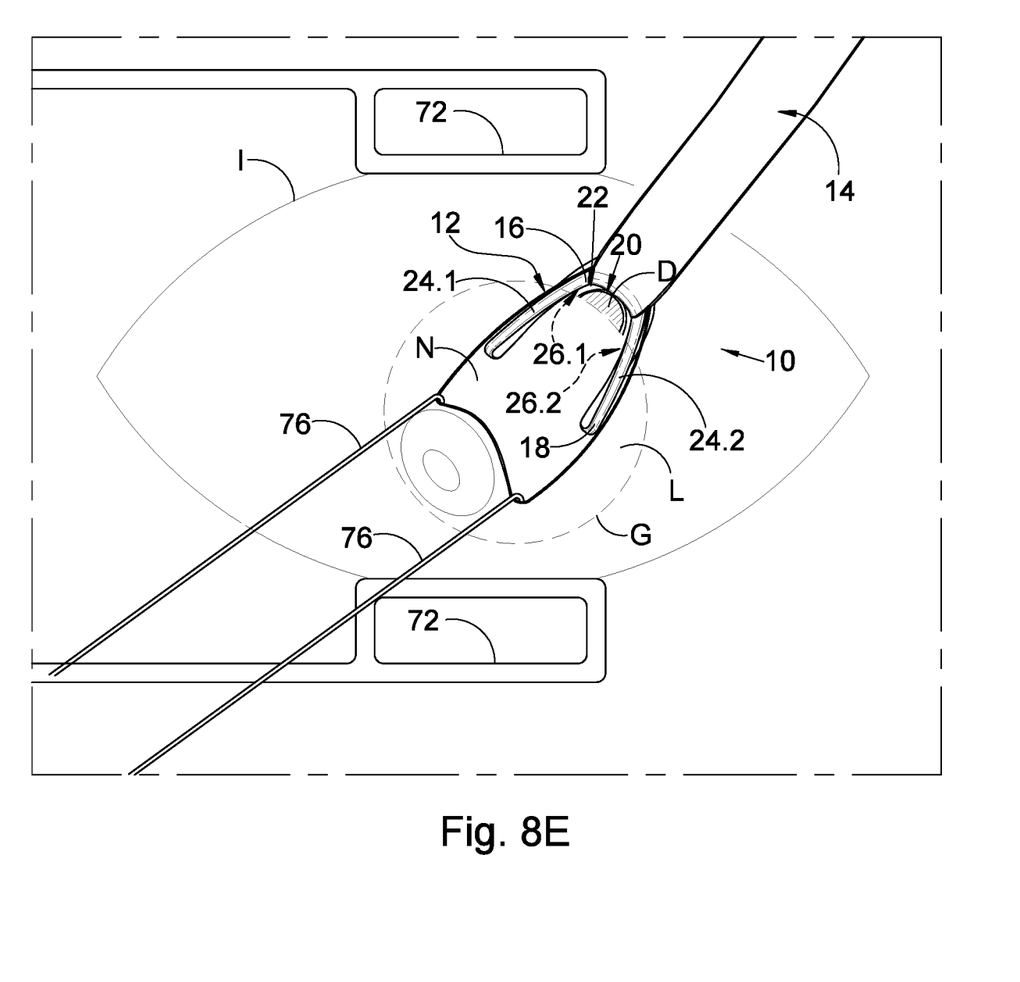

With reference to FIGS. 8A-8E, the manner in which the orbital tissue retractor is used for implanting the head of the shunt into the subarachnoid space, is illustrated. Each eyelid is held open by means of an eyelid speculum 72 and an incision is made in Tenon's capsule G so as to access the Subtenon's space F (see FIG. 8A). Forceps 74 are used to open the Subtenon's space while bridle sutures 76 are used to rotate the eye. The distal end 20 of the orbital tissue retractor 10 is then passed into the Subtenon's space (see FIG. 8B). The tissue retracting device is pushed further into the Subtenon's space such that the curved ocular abutment walls 26.1, 26.2 follow the shape of the ocular globe when the tissue retractor body 12 is advanced towards the optic nerve (see FIG. 8C). The orbital tissue retractor body is then pushed into the Subtenon's space such that the ocular abutment formations 26.1, 26.2 are in abutment with the ocular globe and the optic nerve sheath is received within the concave curved distal end of the tissue retractor body (see FIG. 8D). In this position, direct access to and visualisation of the optic nerve is provided via the internal passageway defined by the orbital tissue retractor body between the orbital connective tissue and the ocular globe and the optic nerve sheath. The orbital tissue retractor body is positioned relative to the ocular globe such that the conjunctiva H is located slightly under the flared collar 18, thereby preventing the conjunctival tissue from prolapsing into the passage and obscuring it. The curved ocular abutment formations rest against the orbital globe minimising distortion of tissues and preventing slippage while allowing access and visualisation of the optic nerve through the passageway. The orbital tissue retractor is manipulated into this position by the handle 14 which is held by a surgeon. In FIG. 8E, a surgeon's view after insertion of the orbital tissue retractor body is shown wherein the cornea L has been rotated.

At this point the surgeon will be able to pass the tissue penetrating tip of the shunt inserting device 30 through the optic nerve sheath under direct visualisation. The shunt 50 can then be advanced into the subarachnoid space, whereafter the shunt inserting device is removed to leave the shunt lying with the distal end in the subarachnoid space.

The Applicant believes that the entire process of positioning the orbital retractor in accordance with the invention will take approximately 10 minutes and will address the above-mentioned difficulties experienced with gaining surgical access to the optic nerve. The process is relatively simple and minimally invasive.

With reference to FIGS. 10 to 14 of the drawings, a second embodiment of an orbital tissue retractor in accordance with the invention, is designated by the reference numeral 100.

In FIGS. 10 to 14 of the drawing, features of the orbital tissue retractor 100 which are the same as and/or similar to those of the orbital retractor 10 are designated by the same and/or similar reference numerals.

The orbital tissue retractor 100 is used for creating a passageway through orbital connective tissue surrounding the ocular globe N and the optic nerve D. The orbital tissue retractor 100 is adapted for use with an endoscope 102 and comprises an orbital tissue retractor body 112 which is formed for abutment with the ocular globe N so as to displace orbital tissue from the orbital globe and define a passageway in the orbital connective tissue for the endoscope 102.

The orbital tissue retractor body 112 has an open proximal end 122 and an open distal end 120. The orbital tissue retractor body has a proximal end section 104 and a distal end section 106 formed integrally therewith.

Figure 10:
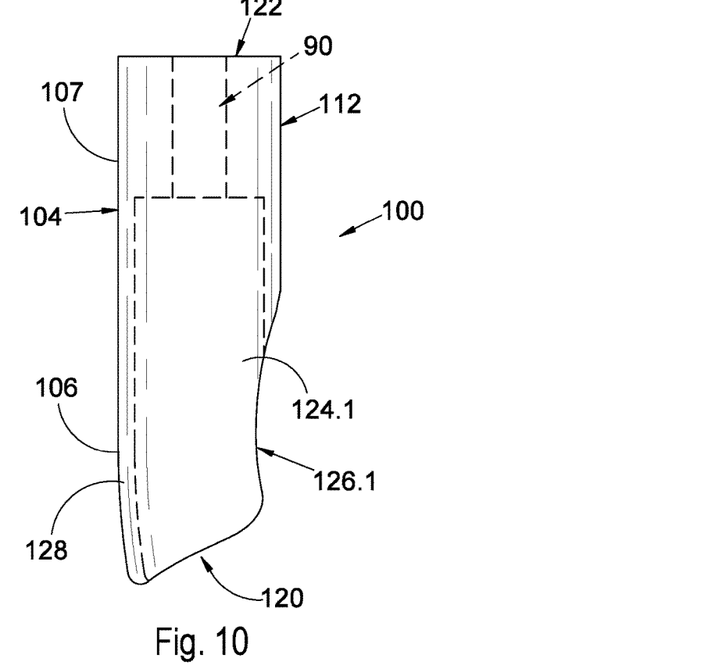
FIG. 10 shows a side view of a second embodiment of an orbital tissue retractor in accordance with the invention.
Figure 14:
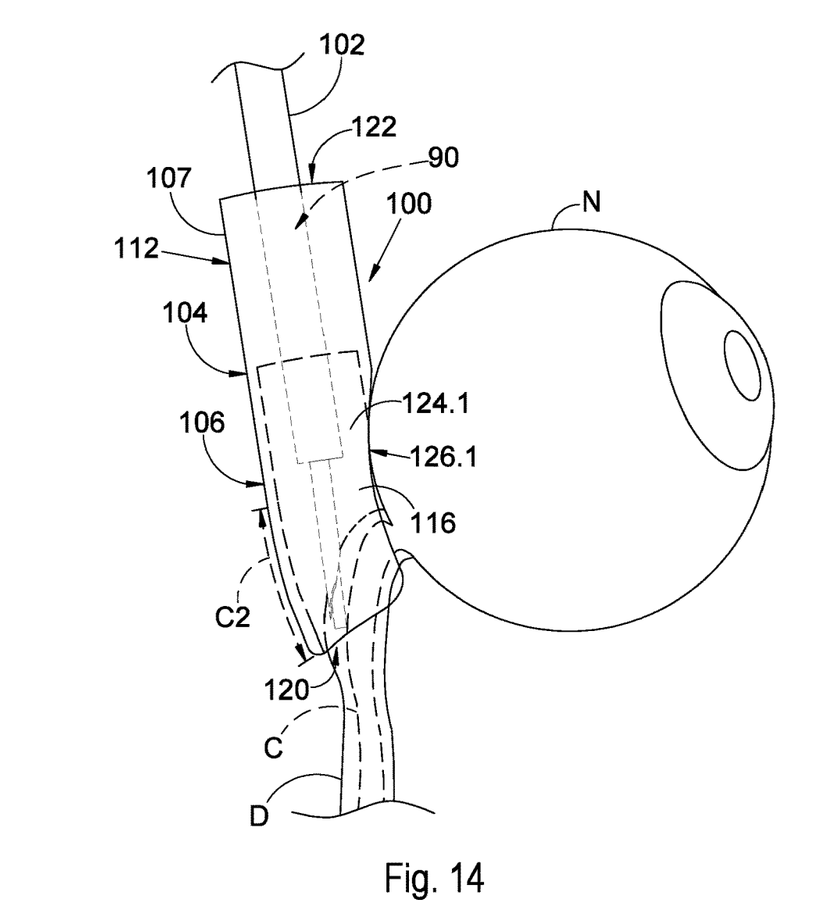
FIG. 14 shows a side view of the orbital tissue retractor of FIG. 10, illustrating the manner in which the orbital tissue retractor is used for supporting an endoscope during a surgical procedure.

The proximal end section 104 comprises a tubular formation 107 which has a hollow tubular configuration. The tubular formation 107 includes a support formation in the form of an internal passage 90 within which the endoscope 102 is received and supported. The internal passage 90 is dimensioned and configured to receive the endoscope therein in a snug supporting arrangement. The internal passage extends from the proximal end of the orbital tissue retractor body in an enlarged area within the distal end section.

Figure 11:
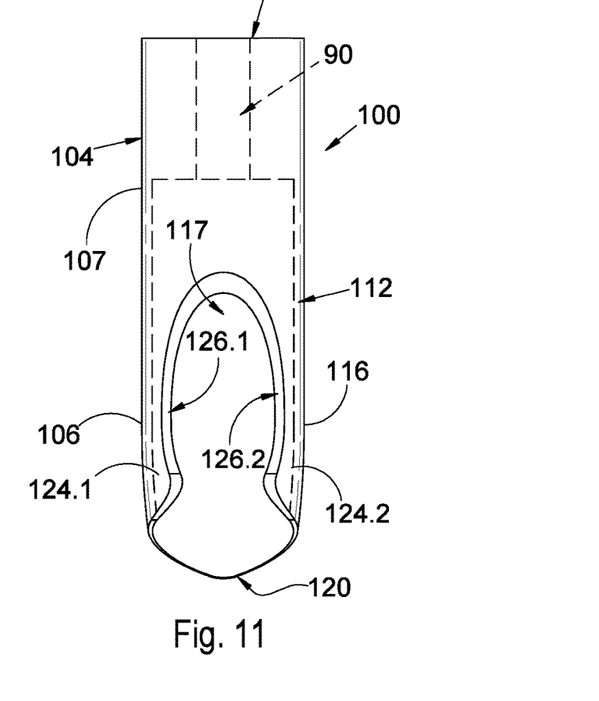
FIG. 11 shows a front view of the orbital tissue retractor of FIG. 10.
Figure 12:
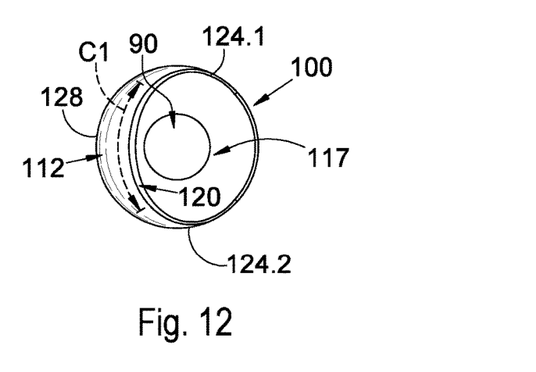
FIG. 12 shows a bottom view of the orbital tissue retractor of FIG. 10.
Figure 13:
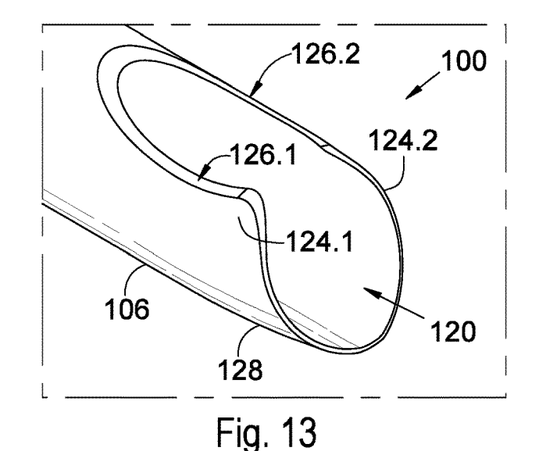
FIG. 13 shows a fragmentary three dimensional view of a distal end region of the orbital tissue retractor of FIG. 10.

The distal end section 106 includes a channel formation 116 having a pair of spaced side wall sections 124.1 and 124.2 and a curved base wall section 128 which extends between the side wall sections. The base wall section 128 has a curved configuration which conforms to an anatomical curvature of the orbit. End regions of the side wall section 124.1, 124.2 define curved ocular abutment formations 126.1 and 126.2, respectively, for abutment with the ocular globe of the eye. More specifically, the base wall section 128 defines a first curved surface C1 extending between the side wall sections 124.1, 124.2, when viewed in cross-sectional end view, which conforms to the anatomical curvature of the orbital rim of the cone-shaped orbit. The base wall section 128 has a second curved surface C2 at a distal end region of the orbital tissue retractor body which, when viewed in side view, conforms to an anatomical curvature of the ocular globe.

The distal end of the tissue retractor body is dimensioned and curved so as to conform to the anatomical shape of the optic nerve sheath D so as to permit the optic nerve sheath to be received and cradled therein.

The orbital tissue retractor in accordance with the invention, provides a clear passageway through orbital tissues to the optic nerve preventing a prolapse of orbital fat into the passageway, while at the same time cradling the optic nerve at the distal end of the retractor.

The invention claimed is:

1. An orbital tissue retractor for use in a surgical operation in the region of an eye socket, the orbital tissue retractor including an orbital tissue retractor body which is formed for abutment with an ocular globe of the eye so as to displace orbital tissue from an orbital globe of an orbit of the eye and which defines a passageway for a surgical instrument between the displaced orbital tissue and the ocular globe, the orbital tissue retractor body having an open proximal end and an open distal end, the orbital tissue retractor body defining a channel formation at least at a distal end region thereof which has a C-shaped configuration when viewed in cross-sectional end view and which is dimensioned and has a curvature so as to conform to a curvature of an optic nerve sheath surrounding an optic nerve, permitting the optic nerve sheath to be received and cradled therein so as to accommodate the optic nerve therein.

2. The orbital tissue retractor as claimed in claim 1, wherein the orbital tissue retractor body is dimensioned so as to be received within the orbit of the eye.

3. The orbital tissue retractor as claimed in claim 1, wherein the orbital tissue retractor body has a curved configuration conforming to an anatomical curvature of the orbit of the eye.

4. The orbital tissue retractor as claimed in claim 1, wherein the channel formation has a pair of spaced side wall sections defining ocular abutment formations for abutment with the ocular globe.

5. The orbital tissue retractor as claimed in claim 4, wherein the ocular abutment formations of the orbital tissue retractor body have curvatures which conform to an anatomical curvature of the ocular globe.

6. The orbital tissue retractor as claimed in claim 4, wherein the channel formation has a base wall section extending between the side wall sections, the base wall section having a first curvature extending between the side wall sections, when viewed in cross-sectional end view, which conforms to an anatomical curvature of an orbital rim of the orbit.

7. The orbital tissue retractor as claimed in claim 6, wherein the base wall section of the channel formation has a second curvature at least at the distal end region of the orbital tissue retractor body, extending in a direction between the proximal and distal ends of the orbital tissue retractor body, when viewed in side view, which conforms to an anatomical curvature of the ocular globe.

8. The orbital tissue retractor as claimed in claim 1, wherein the proximal end of the orbital tissue retractor body is relatively wider than the distal end thereof.

9. The orbital tissue retractor as claimed in claim 8, wherein the orbital tissue retractor body tapers from the proximal end thereof towards the distal end thereof.

10. The orbital tissue retractor as claimed in claim 1, wherein the channel formation of the orbital tissue retractor body extends from the proximal end to the distal end thereof.

11. The orbital tissue retractor as claimed in claim 1, which includes a handle extending from the tissue retractor body which can be held for manipulating the tissue retractor body.

12. The orbital tissue retractor as claimed in claim 11, wherein the handle extends from the proximal end of the tissue retractor body.

13. The orbital tissue retractor as claimed in claim 1, wherein the orbital tissue retractor body includes an outwardly flared collar formation at the proximal end thereof, which is formed so as to prevent conjunctival tissue from prolapsing into the passageway for a surgical instrument and thereby obscuring the passageway, in use.

14. The orbital tissue retractor as claimed in claim 1, wherein the orbital tissue retractor body has a tubular formation having a hollow tubular configuration at a proximal end region thereof, with the distal end region defining the channel formation, the passageway for a surgical instrument being defined by the tubular formation and the channel formation.

15. The orbital tissue retractor as claimed in claim 14, wherein the tubular formation includes a support formation for supporting an endoscope.

16. The orbital tissue retractor as claimed in claim 15, wherein the support formation is in the form of an internal passage within the tubular formation, within which the endoscope is received and supported.

* * * * *